(12) United States Patent
Tsukagoshi et al.

(10) Patent No.: US 8,189,740 B2
(45) Date of Patent: May 29, 2012

(54) X-RAY CT APPARATUS, SCAN PLAN ASSISTANCE APPARATUS AND METHOD FOR SCAN PLAN ASSISTANCE

(75) Inventors: Shinsuke Tsukagoshi, Tochigi-ken (JP); Tetsuya Horiuchi, Saitama-ken (JP); Masahiro Kazama, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 186 days.

(21) Appl. No.: 12/210,811

(22) Filed: Sep. 15, 2008

(65) Prior Publication Data
US 2009/0074143 A1    Mar. 19, 2009

(30) Foreign Application Priority Data
Sep. 14, 2007   (JP) ................. 2007-239585

(51) Int. Cl.
*H05G 1/42*    (2006.01)
(52) U.S. Cl. ........... 378/97; 378/108; 378/165; 378/207
(58) Field of Classification Search ............... 378/4, 16, 378/95, 97, 108–112, 165, 207
See application file for complete search history.

(56) References Cited

U.S. PATENT DOCUMENTS

| | | | | |
|---|---|---|---|---|
| 5,621,779 A | * | 4/1997 | Hughes et al. | 378/65 |
| 2005/0094768 A1 | * | 5/2005 | Ghelmansarai et al. | 378/108 |
| 2006/0293583 A1 | * | 12/2006 | Saracen et al. | 600/407 |
| 2007/0041495 A1 | * | 2/2007 | Olivera et al. | 378/65 |
| 2007/0211857 A1 | * | 9/2007 | Urano et al. | 378/65 |

FOREIGN PATENT DOCUMENTS

JP      2005-185549        7/2005
WO   WO 2007080522 A1 *  7/2007

\* cited by examiner

*Primary Examiner* — Hoon Song
*Assistant Examiner* — Mona M Sanei
(74) *Attorney, Agent, or Firm* — Oblon, Spivak, McClelland, Maier & Neustadt, L.L.P.

(57) ABSTRACT

An X-ray CT apparatus that transmits X-rays toward a subject on the basis of a set scan condition and reconstructs images from detected X-rays that passes through the subject, including a scan plan setting unit configured to set the scan condition, a reference dose storage unit configured to store reference dose information, including an relation between an attribute information about a plurality of kinds of subjects and reference doses to be referenced for an exposure dose, and an exposure dose calculation unit configured to calculate the exposure dose corresponding to the set scan condition in accordance with the timing of setting of the scan condition.

22 Claims, 9 Drawing Sheets

Fig. 1

|  | Weight (kg) | height (cm) | age | CTDI | DLP |
|---|---|---|---|---|---|
| Brain | X≦9.36 | X≦75 | X≦1 | 40<Y | 300<Y |
|  | <X≦19.1 | <X≦109 | <X≦5 | 60<Y | 600<Y |
|  | <X≦33.2 | <X≦138.6 | <X≦10 | 70<Y | 750<Y |
|  | 33.2<X | 138.6<X | 10<X | 60<Y | 1050<Y |

X-RAY CT APPARATUS, SCAN PLAN ASSISTANCE APPARATUS AND METHOD FOR SCAN PLAN ASSISTANCE

CROSS-REFERENCE TO RELATED APPLICATIONS

This application is based upon and claims the benefit of priority from the prior Japanese Patent Application No. 2007-239585, filed Sep. 14, 2007, the entire contents of which are incorporated herein by reference.

BACKGROUND OF THE INVENTION

The conventional X-ray CT (Computed Tomography) apparatus images subjects on the basis of preliminarily set scan conditions. The imaging is executed by emitting X-ray towards the subject and reconstructing signals based on detecting X-ray passed through the subject. Normally, when performing X-ray CT examinations, one examination consists of a plurality of elements, each of which is set for a different body part and has a respective scan condition which reconstruction may be different on an element to element basis. Thus, by reconstruction element is meant units of scan action executed by a single scan condition.

When setting scan conditions, a scan plan assistance apparatus, designed to assist operation of scan planning, is generally used. One scan plan assistance apparatus preliminarily displays a expected value of exposure dose in accordance with a set scan condition (For example, Japanese patent disclosure (Kokai) No. 2005-185549). As the barometer indicating exposure dose, for example, CTDI (Computed Tomography Dose Index) and DLP (Dose Length Product) are used.

The operator can decide whether the planned exposure dose is excessive or not by comparing the exposure dose barometer with reference to an exposure dose value recommended by ICRP (International Commission on Radiological Protection) or IEC (International Electrotechnical Commission).

However, in the actual CT imaging, confirmation of the exposure dose is not necessary and a problem may arise that excess X-rays may be radiated towards the subject. In X-ray CT diagnosis, restraint of exposure dose is a big problem but actual exposure dose decisions are entrusted to operators as mentioned above. Therefore, nowadays, raising operator awareness of exposure dose of an X-ray CT apparatus operator has been a problem.

Furthermore, introduction of area detectors aggravates the problem because opportunities of repeat scan toward same part have increased. Especially, in the case of scanning a patient at risk to radiation, for example, a child, sufficient care is necessary.

BRIEF SUMMARY OF THE INVENTION

An object of the present invention is to provide an X-ray CT apparatus, a scan plan assistance apparatus and a method for scan plan assistance that improves operator awareness of radiation exposure dose.

According to a first aspect of the present invention, there is provided an X-ray CT apparatus that transmits X-rays toward a subject on the basis of set scan condition and reconstructs images from detected X-rays that go through the subject, including a scan plan setting unit configured to set the scan condition, a reference dose storage unit configured to store reference dose information including a relation between attribute information about a plurality of kinds of subjects and corresponding reference dose and an exposure dose calculation unit configured to calculate an exposure dose corresponding to the set scan condition in accordance with the timing of setting of the scan condition.

According to a second aspect of the present invention there is provided a method for scan plan assistance, including setting a scan condition, storing reference dose information including a relation between attribute information about a plurality of kinds of subjects and corresponding reference dose and calculating an exposure dose corresponding to the set scan condition in accordance with the timing of the setting of the scan condition.

According to a third aspect of the present invention there is provided a scan plan assistance apparatus including a scan plan setting unit configured to set a scan condition, a reference dose storage unit configured to store reference dose information including a relation between attribute information about a plurality of kinds of subjects and corresponding reference dose, and an exposure dose calculation unit configured to calculate an exposure dose corresponding to the set scan condition in accordance with timing of the setting of the scan condition.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention wherein:

FIGS. 9(*a*) and 9(*b*) are schematic diagrams indicating examples of the guide screen displayed in a third exemplary embodiment of the X-ray CT apparatus of the invention when the expert plan is made.

DETAILED DESCRIPTION OF THE INVENTION

Referring now to the drawings, where like reference numerals refer to the same or corresponding parts throughout the several views, several exemplary embodiments are next described.

First Exemplary Embodiment

Figure 1:
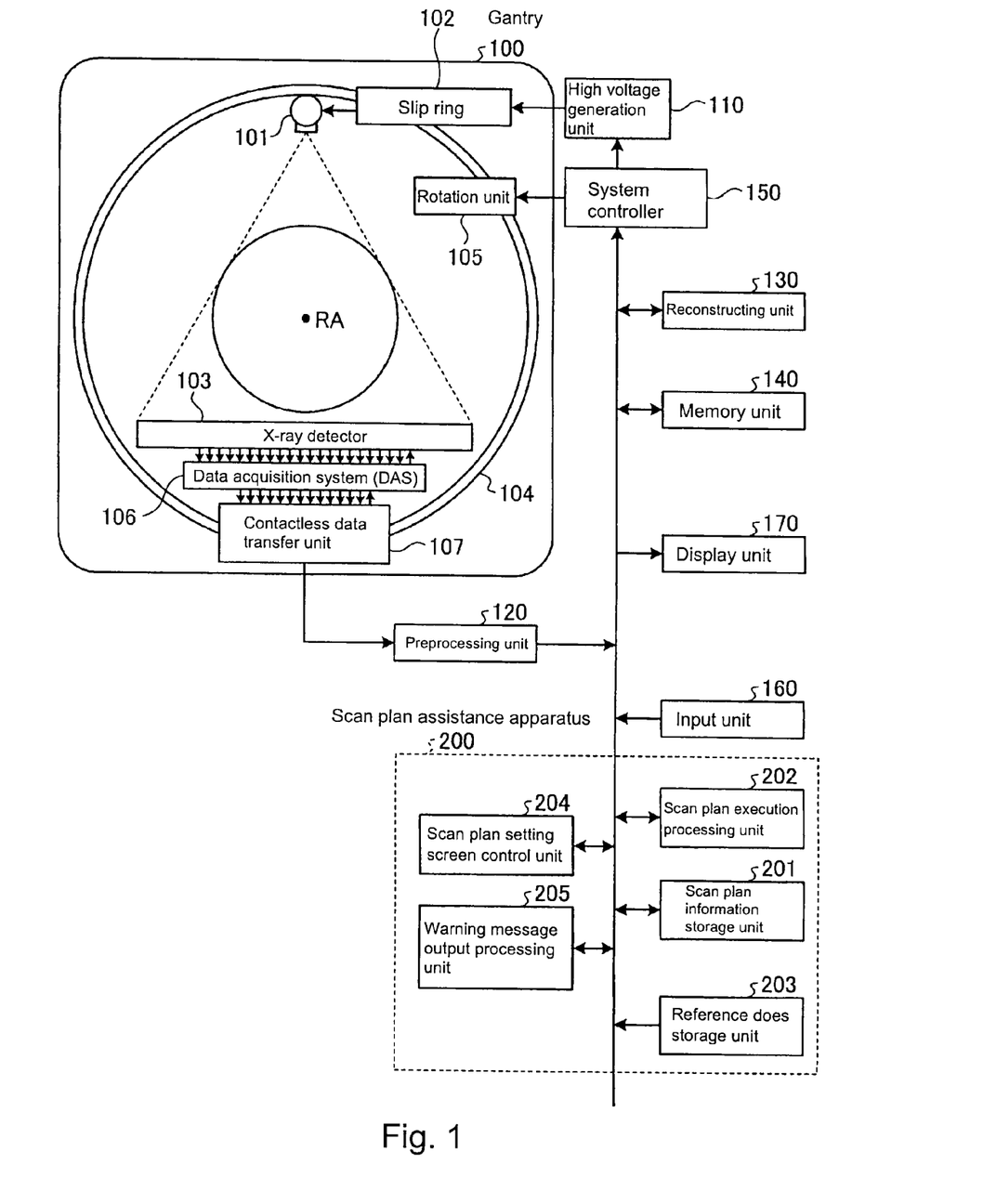
FIG. 1 is a block diagram showing a first exemplary embodiment of an X-ray CT apparatus of the invention.

FIG. 1 is a block diagram showing components of the first exemplary embodiment of an X-ray CT apparatus including a gantry 100, a high voltage generator 110, a preprocessing unit 120, a reconstruction unit 130, a memory unit 140, a system controller 150, an input unit 160, a display unit 170 and a scan plan assistance unit 200.

The gantry 100 emits X-ray toward the subject and generates raw data by detecting X-ray transmitted through the subject. The gantry 100 has an X-ray tube 101, a slip ring 102, an X-ray detector 103, a frame 104, a rotation unit 105, a data acquisition system (DAS) 106 and a contactless data transfer unit 107.

The X-ray tube 101 generates X-ray corresponding to tube voltage and tube current supplied from the high voltage generation unit 110 via the slip ring 102. The X-ray detector 103 detects X-rays generated by the X-ray tube 101 and transmitted through the subject. The X-ray tube 101 and the X-ray detector 103 are located in opposed position so as to hold a subject between the X-ray tube 101 and the X-ray detector 103 and provided on the frame 104 having circle shape.

The frame 104 is rotatably supported and has an axis of rotation RA. The rotation unit 105 drives high speed rotation of the frame 104, for example at a speed of 0.4 second per rotation. The data acquisition system 106 converts X-ray signals detected by the X-ray detection unit 103 into analog voltage signals, amplifies the voltage signal and converts the amplified analog signals into digital signals (raw data). The contactless data transfer unit 107 transmits the raw data outputted from the data acquisition system 106 to the preprocessing unit 120.

The high voltage generation unit 110 supplies the gantry 100 with tube voltage and tube current by which the X-ray tube 101 generates X-rays. The preprocessing unit 120 corrects the raw data supplied from the contactless data transfer unit 107 and generates projection data for image reconstruction.

The reconstructing unit 130 executes predetermined reconstructing processing of the projection data generated by the preprocessing unit 120 and generates image data of the subject. The memory unit 140 stores the projection data generated by the preprocessing unit 120 and the image data reconstructed by the reconstruction unit 130. The system controller 150 controls operations of the X-ray CT apparatus.

The input unit 160 may be a keyboard or a mouse. An operator uses the input unit 160 to enter commands for the X-ray CT apparatus. The display unit 170 is a crystal liquid panel or other conventional display and displays the images reconstructed by the reconstructing unit 130 and scan plan setting screen controlled by after-mentioned scan plan assistance unit 200.

The scan plan assistance unit 200 is designed to assist the scan plan setting operation and includes a scan plan information storage unit 201, a scan plan execution unit 202, a reference dose storage unit 203, a scan plan setting screen control unit 204 and a warning message output processing unit 205.

The scan plan information storage unit 201 stores scan conditions of elements included in the scan plan set by the operator. One scan condition corresponds to one element. The scan plan execution unit 202 controls the system controller 150 in the gantry 100 on the basis of the scan conditions and executes scanning on the basis of the scan plan set by the operator.

The reference dose storage unit 203 stores reference dose information that corresponds to attribute information of the subject. The reference dose is a reference value of exposure dose. More particularly, the reference dose information includes information related to attribute information (body weights, body heights and ages) and reference dose indicated by CTDI and DLP categorized for each of plural body parts.

Figure 2:
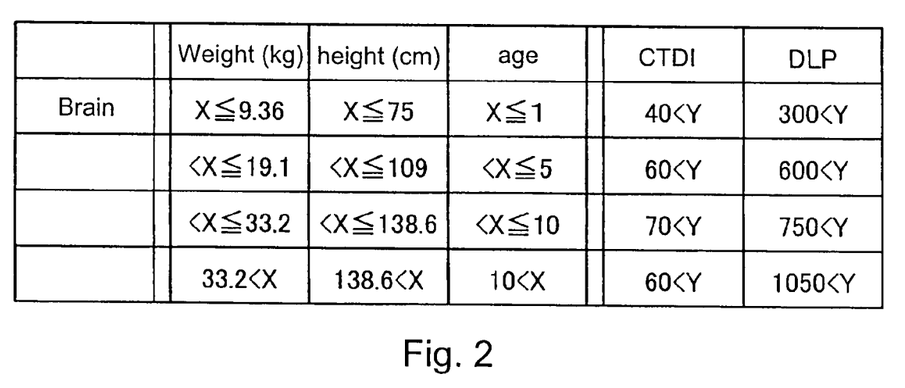
FIG. 2 is a diagram indicating an example of reference dose information stored in the reference dose storage unit of the first exemplary embodiment of the X-ray CT apparatus of the invention.

FIG. 2 is a diagram indicating an example of reference dose information stored in the reference dose storage unit 203. The diagram indicates an example of reference dose information about the brain. For example, the reference dose storage unit 203 stores the information that reference dose is 60 at CTDI or 600 at DLP in case the body weight is 9.36 Kg or under and the body height is 75 cm or under and age of the subject is 1 year or under, as shown in the diagram. The reference dose storage unit 203 may preliminarily store other reference values of exposure dose recommended by various academic conferences, for example ICRP or IEC.

Referring again to FIG. 1, the scan plan setting screen control unit 204 displays scan plan setting screen on the display device and executes control of the display of the scan plan setting screen. The scan plan setting screen is an interface screen for receiving and viewing operation of setting scan plan and scan condition.

Figure 3:
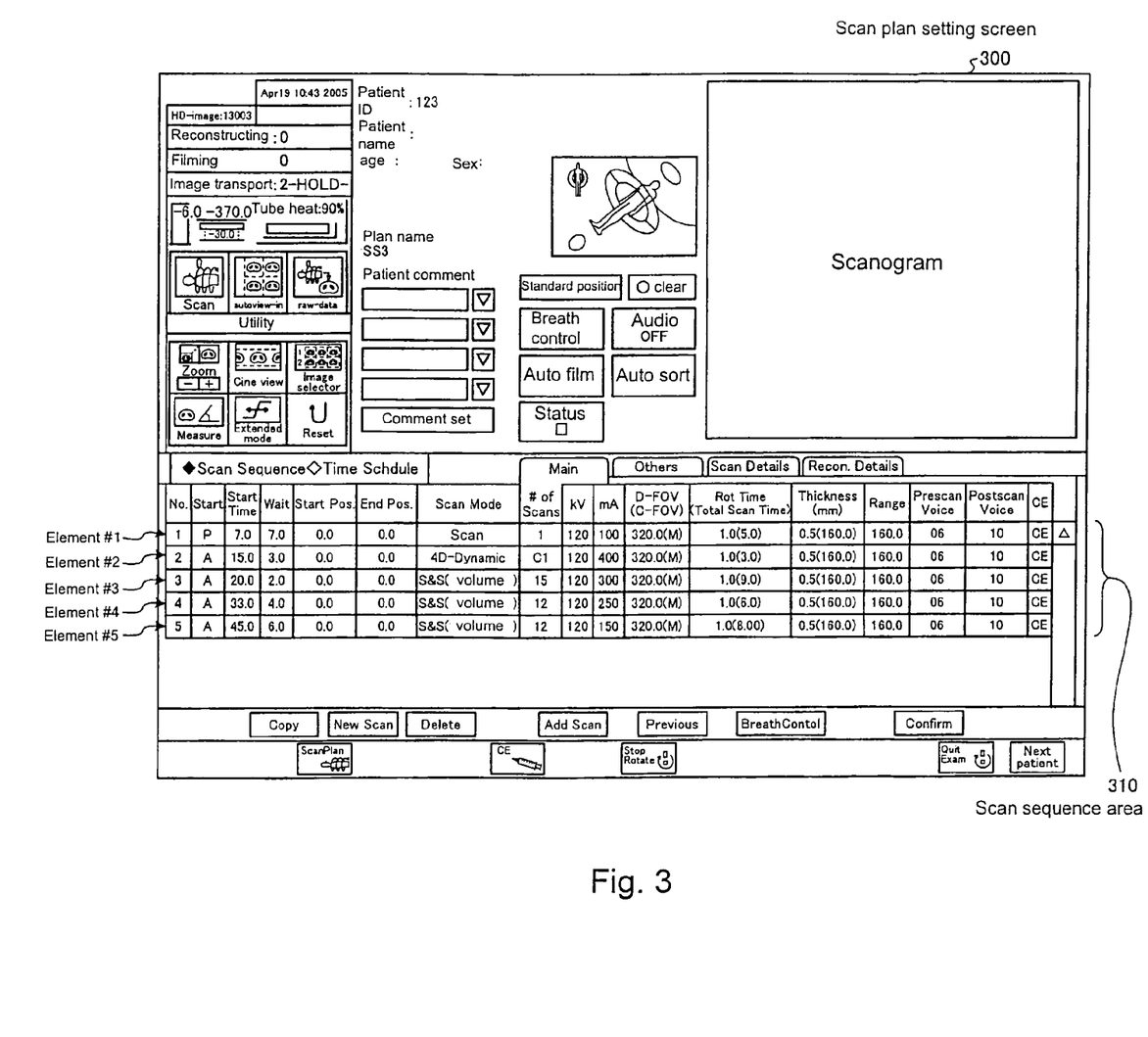
FIG. 3 is a diagram indicating an example of a scan plan setting screen displayed by the scan plan setting control unit of the first exemplary embodiment of the X-ray CT apparatus of the invention.

In accordance with a requested operation, the scan plan setting screen control unit 204 displays the scan plan setting screen. FIG. 3 is a diagram indicating an example of a scan plan setting screen displayed by the scan plan setting control unit 204. As the diagram shows, the scan plan setting screen control unit 204 displays a scan plan setting screen 300 on which is allocated patient information, utility information, a thermal limit of the X-ray tube and scanogram as basic information, and scan sequence area 310.

The scan sequence area 310 is an area in the screen 300 for setting scan conditions about the subject's part. For example, the scan sequence area 310 is composed in table format and configured to input a plurality of elements (for example, element #1 to #5 shown in the diagram) about one part. About each of the elements, items shown below can be inputted as scan condition.

Scan element No. (Shown as "No." in the diagram)
Start class. (Shown as "Start" in the diagram)
Start time corresponding to past time from trigger of scan start about each of the elements. (Shown as "Start Time" in the diagram)
Wait time corresponding to interval from an end of last element to a start of current element. (Shown as "Wait" in the diagram)
Scan start position. (Shown as "Start Pos." in the diagram)
Scan end position. (Shown as "End Pos." in the diagram)
Scan mode indicating a kind of scan. (Shown as "Scan Mode" in the diagram)
Scan number of times. (Shown as "# of Scans" in the diagram; in the scano mode, dynamic mode and helical mode, "1" or "C1" is set and in the S & S mode, "I5" and all that. "1" or "C1" indicates generating X-ray continuously while element period and "I5" indicates generating X-ray pulse 5 times at regular intervals.)
Tube voltage. (Shown as "kV" in the diagram)
Tube current. (Shown as "mA" in the diagram)
Diameter of reconstruction view. (Shown as "D-FOV." in the diagram)

Scan time for 360-degree roll of the X-ray tube. (Shown as "Rot time" in the diagram)

Total scan time. (Shown as "Total Scan Time" in the diagram; in scano mode, dynamic mode and helical mode, the time is simply given by the time of generating X-ray. In S & S mode, the times given by Rotation time multiplied by scan number plus rest time multiplied by rest number.)

Imaging thickness. (Shown as "Thickness" in the diagram)

Therefore a scan condition is inputted to the scan sequence area of the scan plan setting screen 300 and predetermined operation for scan execution order makes the scan plan setting screen control unit 204 to calculate exposure dose in the case that scan is executed in accordance with inputted scan condition. In particular, the scan plan setting screen control unit 204 calculates CTDI and DLP about the subject part (sum of the CTDI values and DLP values calculated about a plurality of the elements) and calculates sum of DLP of current examination including scan of the other subject parts.

On the other hand, the scan plan setting screen control unit 204 refers to the reference dose stored in the reference dose storage unit 203 and obtain a reference dose value in accordance with the attribute information (body weight, height or ages) of the subject. In particular, the scan plan setting screen control unit 204 obtains CTDI and DLP about a subject part as the reference dose value, obtains DLP about all of subject parts in current examination and calculates sum of the DLP values.

Therefore, after calculation of the exposure dose and the reference dose, the scan plan setting screen control unit 204 compares calculated exposure dose CTDI and DLP and the sum of DLP with the obtained reference dose CTDI and DLP and sum of DLP, respectively.

In the case that all of the exposure dose values do not exceed the reference dose values, the scan plan setting screen control unit 204 stores the scan conditions inputted in the scan sequence area 310 into the scan plan information storage unit 201 and commands the scan plan execution unit 202 to execute scans.

On the other hand, if at least one of the calculated exposure dose exceeds the reference dose, the scan plan setting screen control unit 204 commands a warning message output processing unit 205, discussed below, to output a warning message. In the case that warning message is commanded, after a further operation of executing scans, the scan plan setting screen control unit 204 stores the scan conditions inputted in the scan sequence area 310 into the scan plan information storage unit 201 and commands the scan plan execution unit 202 to execute scans.

Returning to FIG. 1, the warning message output processing unit 205 outputs a warning message on command received from the scan plan setting screen control unit 204. Upon receiving a command to output a warning message from the scan plan setting screen control unit 204, the warning message output processing unit 205 outputs a message indicating the exposure dose calculated by the scan plan setting screen control unit 204 (exposure dose in the case of set scan conditions) and reference dose obtained by the scan plan setting screen control unit 204 (reference dose corresponding to the attribute information of the subject) for display on the scan plan setting screen.

Figure 4:
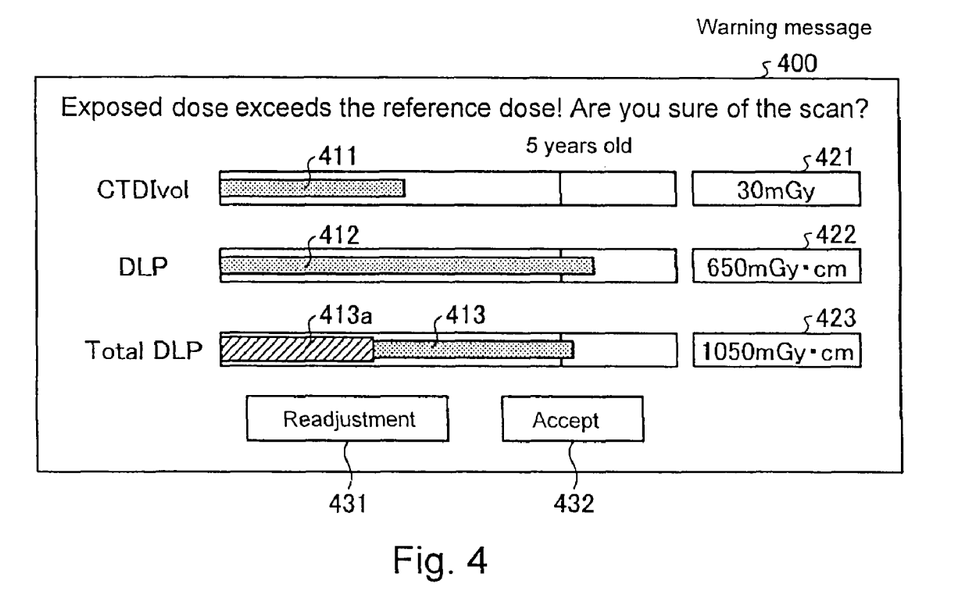
FIG. 4 is a diagram indicating an example of warning message outputted by the warning message output processing unit of the first exemplary embodiment of the X-ray CT apparatus of the invention.

FIG. 4 is a diagram indicating an example of warning message output by the warning message output processing unit 205. For example, the warning message output processing unit 205, as shown the diagram, may output bar charts 411, 412 and 413 indicating a relation between the amount of the exposure dose and the amount of the reference dose, exposure dose values 421, 422 and 423 and a scan warning message 400 including a condition readjustment button 431 and an accept button 432 with a confirmation text message indicating whether the set scan condition is acceptable or not.

The bar chart 411 indicates exposure dose CTDI, the bar chart 412 indicates exposure dose DLP and the bar chart 413 indicates sum of DLP of current examination (Total DLP). The value 421 is exposure dose value CTDI, value 422 is exposure dose value DLP and value 423 is sum of exposure dose value DLP of a current examination.

As mentioned above, it is enabled to show the operator expressly how exposure dose exceeds the reference dose by outputting the bar charts 411, 412 and 413 indicating the relation between the amount of the exposure dose and the amount of the reference dose.

Furthermore, the warning message output processing unit 205 refers to the scan condition stored in the scan plan information storage unit 201, calculates the sum of DLP in the past examination of same subject and displays the bar chart 413*a* indicating the past sum of DLP, adding to the bar chart 413 an indication of the current examination sum of DLP. In this case, the warning message output processing unit 205 displays the bar charts 413 and 413*a* in colors or patterns different from each other.

In this case, because the warning message output processing unit 205 outputs bar charts 413*a* indicating the past examination sum of DLP, the operator is enabled to consider the current examination exposure dose in comparison with the past examination exposure dose.

Returning to explanation of the warning message 400, the scan condition readjustment button 431 and the accept button 432 are buttons for receiving a selection of an operator readjusting scan condition or accepting scan on a set scan condition.

Therefore, in the case that the operator pushes the scan condition readjustment button 431, the warning message output processing unit 205 stops display of the warning message 400 and returns to an input status by which scan conditions can be entered into scan plan setting screen 300. On the other hand, in the case that the operator pushes the accept button 432, the warning message output processing unit 205 instructs the scan plan setting screen control unit 204 to continue scan by the set scan conditions.

Because the warning message output processing unit 205 receives the operator's selection of readjusting the scan condition or accepting scan on the set scan condition by means of the scan condition readjustment button 431 and the accept button on the warning message, it is enabled that the operator can decide whether the scan should be executed or not on the confirmation of the information from the warning message output processing unit 205.

In addition, the warning message 400 output from the warning message output processing unit 205 is not limited to that as mentioned above. For example, in this explanation, bar charts are shown as indicators of exposure dose, but other kinds of graphs or displays by which the operator can perceive the relative amount of exposure dose and reference dose, may be used.

Furthermore, in the above explanation, bar charts can be distinguished by using respective colors, but other visual devices which distinguish the bar charts from each other or different display manners, for example different patterns, may be used.

In addition, in this explanation, the bar chart 413 indicating DLP on current examination is added to the bar chart 413*a* indicating DLP on past examination. However the bar charts may be displayed up and down.

Figure 5:
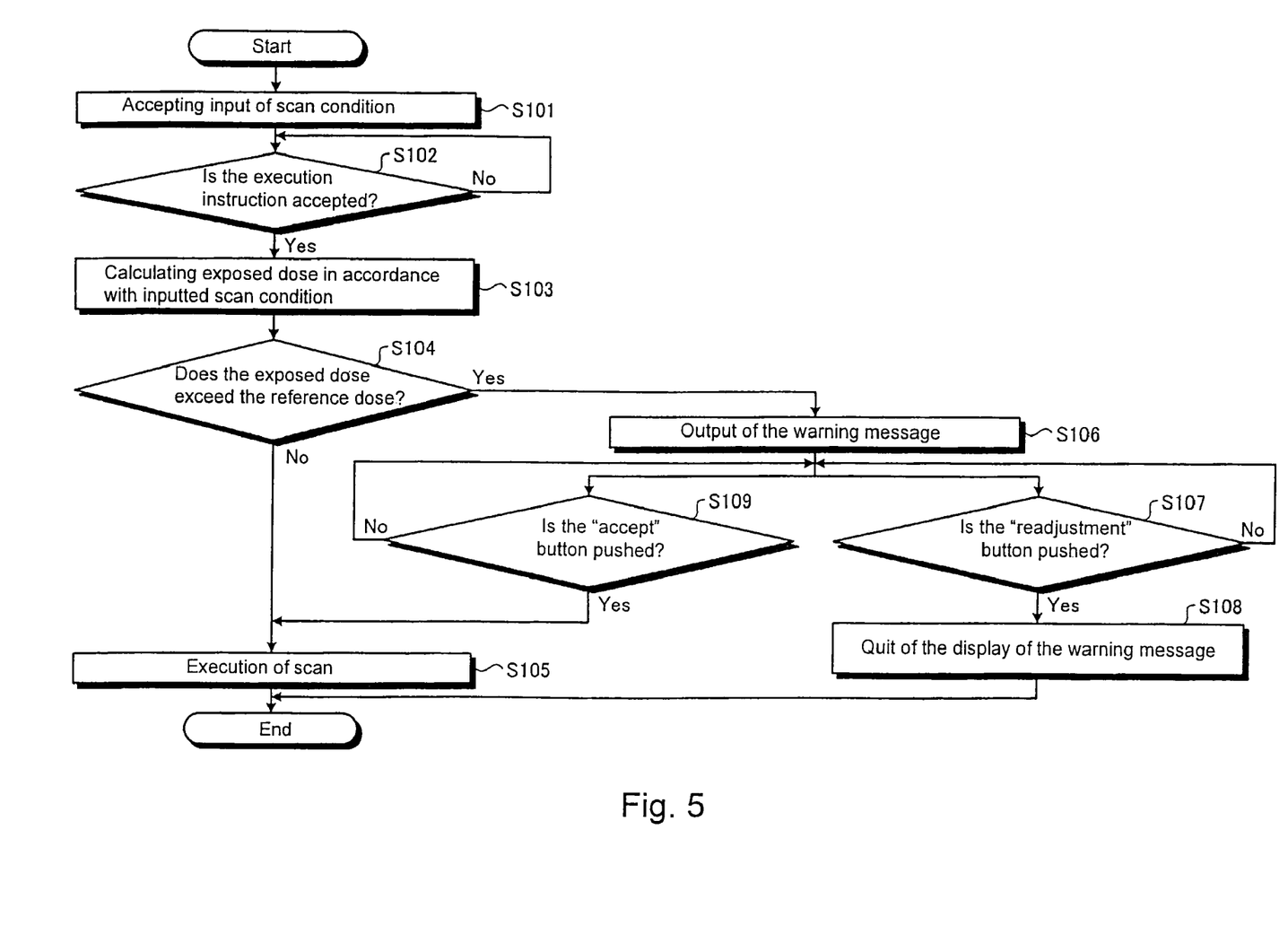
FIG. 5 is a flow chart indicating procedures of the first exemplary embodiment of the X-ray CT apparatus of the invention.

Next, procedures of the first exemplary embodiment of X-ray CT apparatus are explained by reference to the flow chart shown in FIG. 5. As shown in the flow chart, on this X-ray CT apparatus, the scan plan setting screen control unit 204 receives input of scan condition from the operator by the scan plan setting screen 300 (Step S1) and calculates exposure dose on the basis of the inputted scan condition (Step S103) after receiving a scan execution instruction (Step S102, Yes).

In the case that the calculated exposure dose does not exceed the reference dose in accordance with the attribute information of the subject (Step S104, No), the scan plan execution unit 204 instructs the scan plan execution processing unit 202 to execute the scan. In accordance with this instruction, the scan plan execution processing unit 202 executes the scan (Step S105).

On the other hand, in the case that the calculated exposure dose exceeds the reference dose in accordance with the attribute information of the subject (Step S104, Yes), the scan plan setting screen control unit 204 instructs the warning message output processing unit 205 to output a warning message. In that case, the warning message output processing unit 205 outputs a warning messages 400 on the scan plan setting screen 300 (Step S106).

Thereafter, in the case that the operator pushes the condition readjustment button 431 (Step S107, Yes), the warning message output processing unit 205 ceases the display of the warning message 400 (Step S108), whereupon the scan plan assistance unit 200 returns to the available state for inputting scan conditions from the scan plan setting screen 300.

On the other hand, in the case that the operator pushes the accept button 432 (Step S109, Yes), the warning message output processing unit 205 instructs the scan plan setting screen control unit 204 to execute scanning. The scan plan execution unit 204 instructs the scan plan execution processing unit 202 to execute scanning, whereupon the scan plan execution processing unit 202 executes scanning (Step S105).

As mentioned above, in this first exemplary embodiment, the reference dose storage unit 203 stores reference dose information corresponding to attribute information about the subject. On the other hand, when the operator sets scan conditions, the scan plan setting screen control unit 204 refers to the reference dose information stored in the reference dose storage unit 203 and decides whether or not the exposure dose in the case that X-ray is transmitted in accordance with the set scan condition exceeds the reference dose corresponding to the subject's attribute information. Therefore, the warning message output processing unit 205 outputs warning message when the scan plan setting screen control unit 205 decides that the exposure dose exceeds the reference dose. In this manner, the X-ray CT apparatus related to the first exemplary embodiment makes it possible to remind the operation with the requisite information to decide appropriate amounts of dose exposure.

Second Exemplary Embodiment

In the first exemplary embodiment described above, a warning message is outputted in accordance with a check of the exposure dose corresponding to scan by a set scan condition after an executing instruction from the operator is accepted. However, for example, while the operator sets the scan condition, whether or note the exposure dose exceeds reference dose may be informed by predetermined interfaces.

Therefore, as a second exemplary embodiment explained below, exposure dose corresponding to set scan condition is displayed and a dose display button provided so as to inform of excessive exposure dose in relation to the reference dose by the changing display color on the scan plan setting screen 300. Components of the X-ray CT apparatus related to the second exemplary embodiment are basically same as the components explained reference to FIG. 1 and only the scan plan setting screen control unit 204 and the warning message output processing unit 205 in the scan plan assistance apparatus are different. Therefore these two processing units are explained below.

Figure 6:
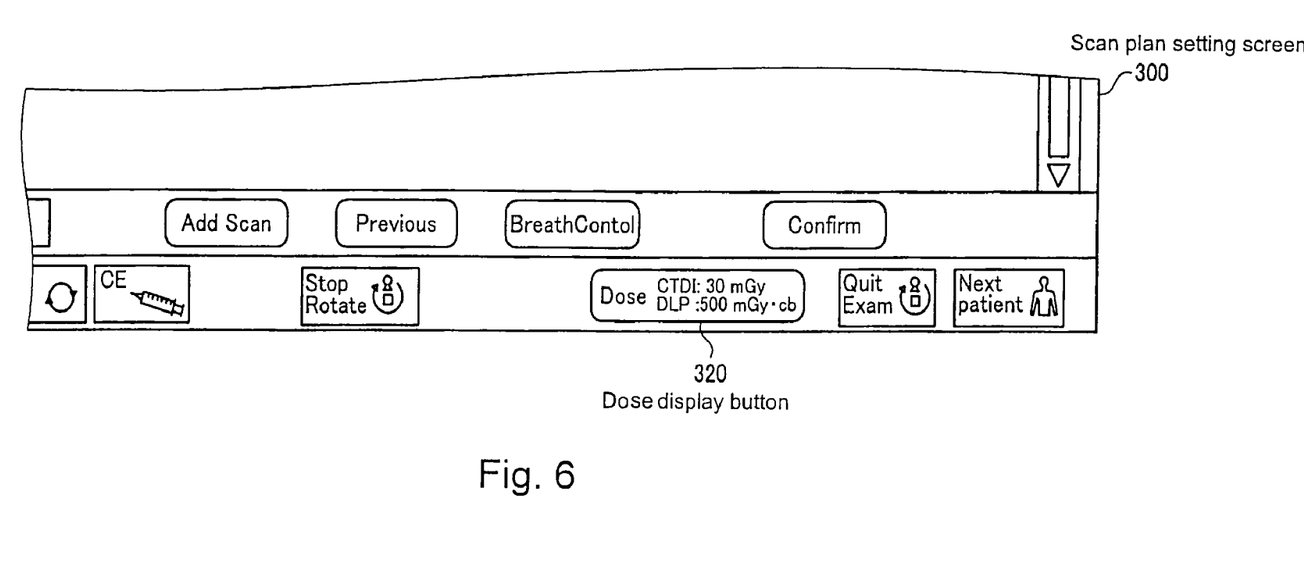
FIG. 6 is a schematic diagram indicating an example of the dose display button located on the scan plan setting screen of a second exemplary embodiment of the X-ray CT apparatus of the invention.

In the second exemplary embodiment, the scan plan setting screen control unit 204 locates the dose display button at a predetermined position and outputs scan plan setting screen 300. FIG. 6 is a schematic diagram indicating an example of the dose display button 320 located on the scan plan setting screen 300. For example, the scan plan setting screen control unit 204, as shown in the diagram, locates the dose display button 300 displaying CTDI and DLP on a bottom position in the scan setting screen 300. Each of CTDI and DLP indicates exposure dose corresponding to the case that X-ray is transmitted in accordance with the scan condition inputted in the scan sequence area 310.

When each element of the scan condition is inputted in the scan sequence area, the scan plan setting screen control unit 204 calculates exposure dose corresponding to the set scan condition and displays the calculated exposure dose on the dose display button 320. In particular, the scan plan setting screen control unit 204 calculates CTDI and DLP (the sum of the CTDI and DLP calculated in accordance with scan condition set about each element) of the subject part and the sum of DLP of current examination including the other parts and displays the calculated CTDI and DLP on the dose display button 320.

As explained above, because the scan plan setting screen control unit 204 calculates exposure dose in accordance with inputted scan condition and displays the calculated exposure dose on the dose display button 320, it is possible to inform the operator about exposure dose of the subject whenever scan condition is set.

The scan plan setting screen control unit 204 also obtains the value of the reference dose corresponding to attribute information of the subject (height, weight or age) by reference to the reference dose information in the reference dose storage unit 203. In particular, as a value of reference dose, the scan plan setting screen control unit 204 obtains CTDI and DLP of each part and DLP of all of subject parts of current examination and calculates a sum of the obtained DLP.

After calculation of the exposure dose and the reference dose, the scan plan setting screen control unit 204 compares the calculated exposure dose CTDI, DLP and sum of DLP to obtain the reference dose CTDI, DLP and sum of DLP respectively.

In the case that exposure dose does not exceed the reference dose, the scan plan setting screen control unit 204 displays blue dose display button 320. On the other hand, in the case that exposure dose exceeds the reference dose, the scan plan setting screen control unit 204 change the display color of the dose display button 320, and a red dose display button is displayed.

The scan plan setting screen control unit 204 not only controls display colors of the dose display button but also instructs the warning message output processing unit 205 to output a warning message when the operator pushes the dose display button 320. The scan plan setting screen control unit 204 always accepts input by pushing of the dose display button 320 by the operator.

In the second exemplary embodiment, the warning message processing unit 205, when the scan plan setting control unit 204 instructs the warning message processing unit 205 to output a warning message, outputs the warning message indicating the exposure dose calculated by the scan plan setting screen control unit the (corresponding to a scan in accordance with set scan condition) and the reference dose obtained by the scan plan setting screen control unit 204 (corresponding to attribute information of the subject) on the scan plan setting screen 300.

Figure 7:
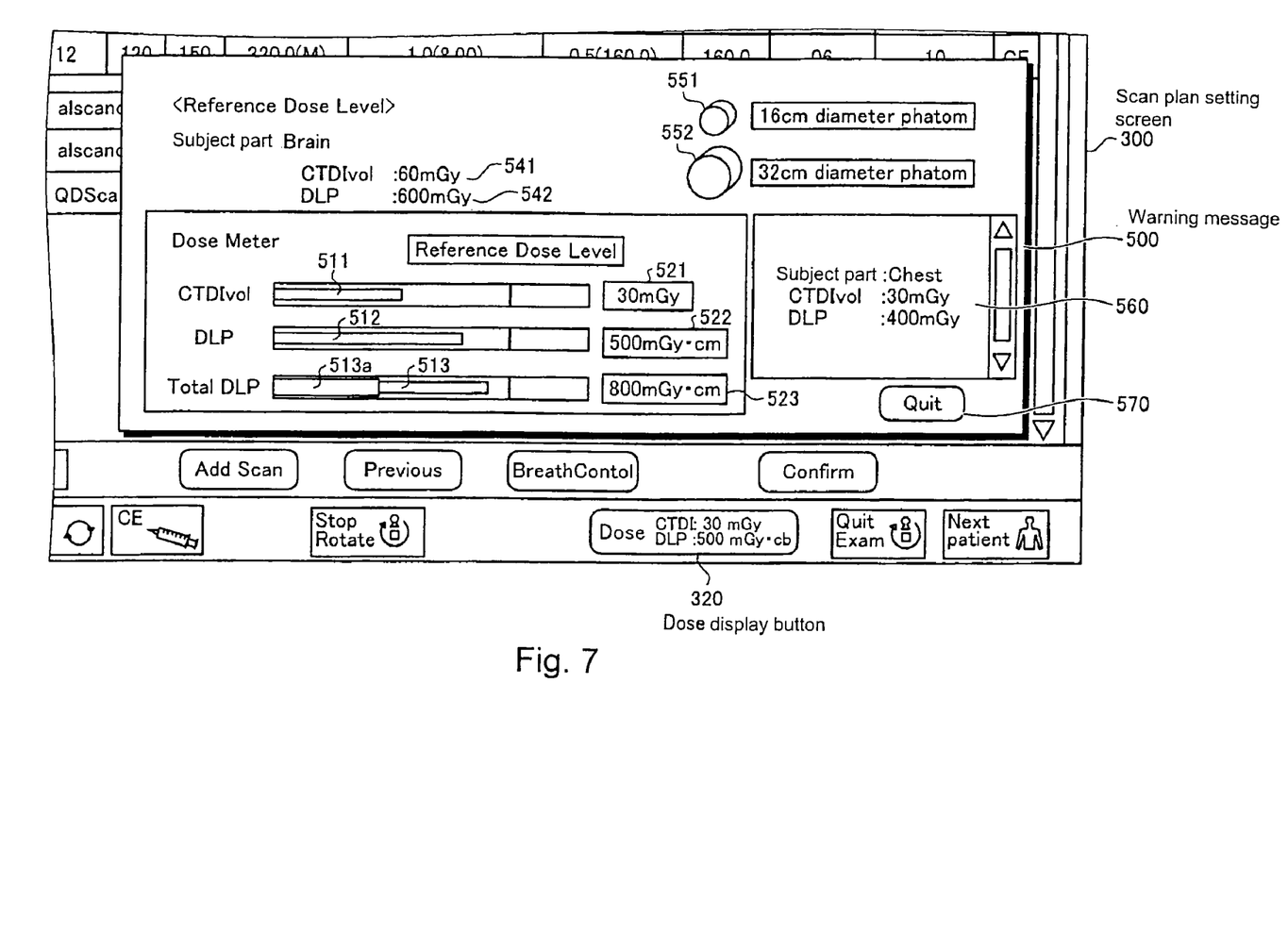
FIG. 7 is a schematic diagram indicating an example of the warning message displayed by the warning message output processing unit of the second exemplary embodiment of the X-ray CT apparatus of the invention.

FIG. 7 is a schematic diagram indicating an example of the warning message displayed by the warning message output processing unit 205 related to the second exemplary embodiment. For example, the warning message output processing unit 205 outputs a warning message 500 including a subject part, a reference dose 541 and 542, exposure dose on phantom 551 and 552, bar charts 511, 512 and 513 each of which indicates amounts of the exposure dose compared to the reference dose, values of the exposure dose 521, 522, 523, scan history information 560 and a quit button 570.

The reference dose 541 is a value of the CTDI of the reference dose calculated by the scan plan setting screen control unit 204. The reference dose 542 is a value of the DLP of the reference dose calculated by the scan plan setting screen control unit 204. The exposure dose on phantom 551 is a graphic indicating that each of kinds of dose are based on the dose measured by the 16 cm phantom. The exposure dose on phantom 552 is a graphic indicating that each kind of dose is based on the dose measurer by the 32 cm phantom.

The bar chart 511 indicates exposure dose CTDI, the bar chart 512 indicates exposure dose DLP and the bar chart 513 indicates sum of DLP (Total DLP) of current examination. The value 521 is a value of exposure dose CTDI, the value 522 is a value of exposure dose DLP and the value 523 is a value of sum of DLP of current examination. Furthermore, the warning message output processing unit 205 refers to the scan condition stored in the scan plan information storage unit 201, calculates the sum of DLP in the past examination of same subject and displays the bar chart 513a indicating the past sum of DLP, adding to the bar chart 513 an indication of the current examination sum of DLP. In this case, the warning message output processing unit 205 displays the bar charts 513 and 513a in a manner different from each other, so that an operator is able to compare the current examination exposure dose with the past examination exposure dose.

The scan history information 560 indicates history of scans that already done. When the warning message output processing unit 205 outputs the warning message 500, because the scan history information 560 is also displayed, the operator can set the current scan condition in consideration of past exposure dose of the subject.

The warning message output processing unit 205 displays the warning message 500 mentioned above on the scan plan setting screen 300 whenever the scan plan setting screen control unit 204 instructs the warning message output processing unit 205 to output a warning message in accordance with pushing of the dose display button 320 by the operator.

Figure 8:
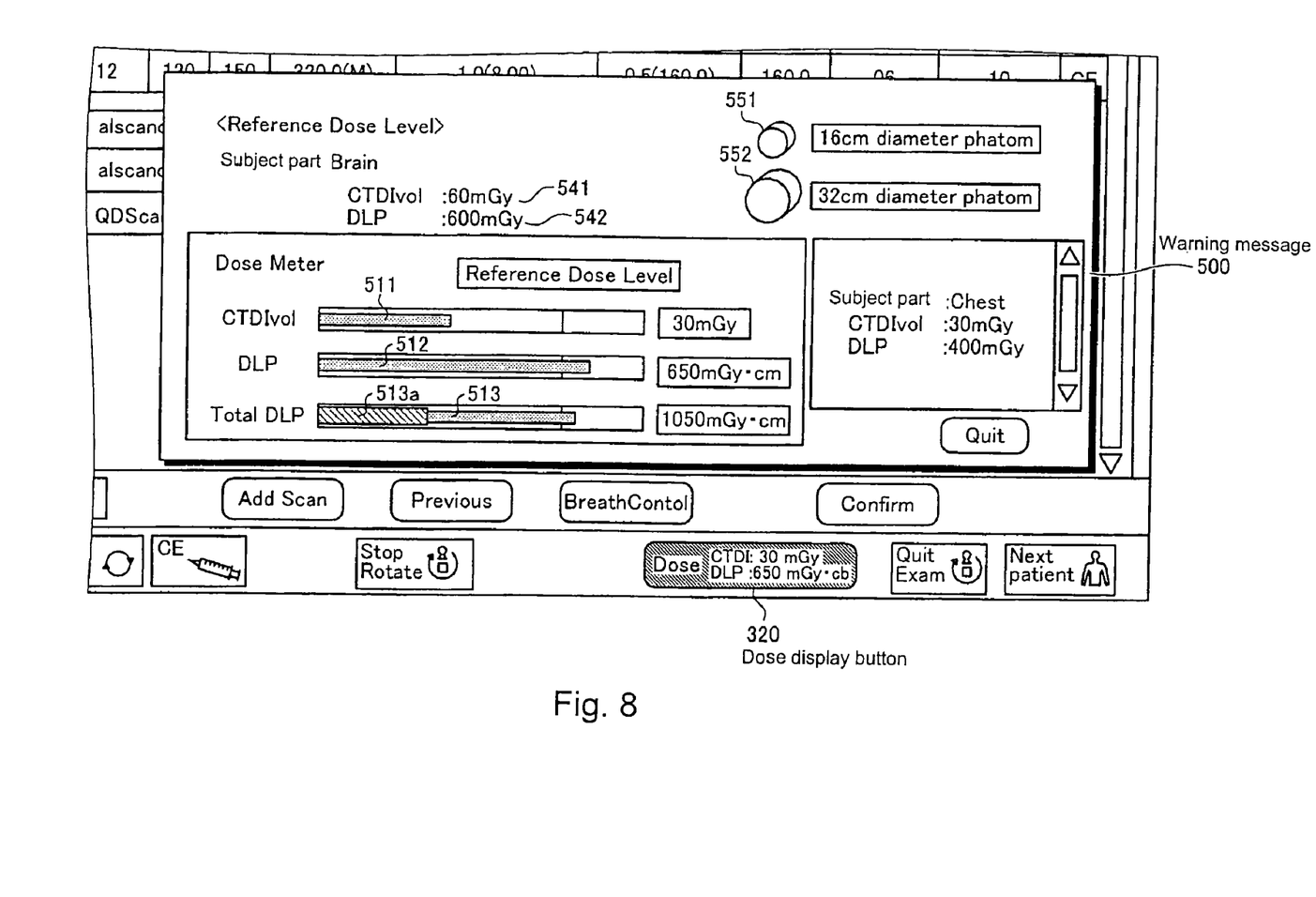
FIG. 8 is a schematic diagram indicating an example of the warning message of the second exemplary embodiment of the X-ray CT apparatus of the invention in the case that the exposure dose exceeds the reference dose.

FIG. 8 is a schematic diagram indicating an example of the warning message 500 in the case that the exposure dose exceeds the reference dose. As the diagram shows, for example, in the case that exposure dose DLP corresponding to the set scan condition exceeds the reference dose, the color of the dose display button 320 is changed and bar chart 512 displayed on the warning message at that time indicates that the exposed DLP exceeds the reference dose. In this example, a reference dose labels indicating each position of the reference dose on the bar charts of CTDI, DLP and sum of DLP (Total DLP) is displayed on the screen.

In this manner, the warning message processing unit 205 changes the color of the dose display button and displays bar charts indicating amounts of the exposure dose in comparison to the reference dose. Therefore, the operator can perceive any excess of the exposure dose visually.

In addition, because the warning message output processing unit 205 outputs the warning message 500 when the operator pushes the dose display button 320, the opportunity to consider the amount of the exposure dose in comparison to the reference dose can be always provided while the operator sets the scan condition.

As above described, the exposure dose history information of the current examination is only displayed. However the entire history of the subject's exposure doses in all past examinations may be displayed. In this manner, the exposure dose may be calculated from past scan conditions stored in the scan plan information storage unit 201 or from a distributed memory device personally owned by the subject and which stores information of the subject's past examinations. In this manner, the operator can set a scan condition of a current examination in consideration of the accumulated history of past exposure dose in past examinations.

As the mentioned above, in this second exemplary embodiment, because the color of the dose display button 320 is changed at the moment that the exposure dose exceeds the reference dose, the operator can quickly and easily perceive the excess of the exposure dose at the moment of the excess while the operator sets scan conditions.

In addition the change of the color of the dose button 320 is not limited from red to blue. Another visual device of display of the dose button 320, for example changing from another color to another color or from blinking display to non-blinking display, may be fine.

Third Exemplary Embodiment

A third exemplary embodiment employs a scan plan assistance apparatus for X-ray CT apparatus that selects and provides the most appropriate scan plan for the operator from a plurality of pre-registered scan plans in accordance with attribute information (sex, age, body shape) of the subject or part to be imaged. The pre-registered scan plans are generally known and called "Expert plans" and made by experts having that high expert knowledge about X-ray CT scan.

In the making of the expert plan, the reference dose information makes it possible that attribute information of a subject suitable for the exposure dose corresponding to the set scan condition is provided as reference information when the expert input scan condition for the expert plan is decided.

Therefore, as the third exemplary embodiment, when the expert plan is decided, the case that attribute information suitable for an exposure dose corresponding to the inputted scan condition as reference information on the basis of the reference dose information stored in the reference dose storage unit 203 is explained below.

In the third exemplary embodiment, the scan plan assistance unit 200, when the operator (the above mentioned "expert") inputs scan condition, calculates values of exposure dose from the inputted scan condition and outputs a guide screen displaying the calculates values on the display unit 170. The scan plan assistance unit 200 outputs also the guide screen so that the operator can realize what attribute information of the subject is suitable for the calculated value of the exposure dose.

Figure 9A:
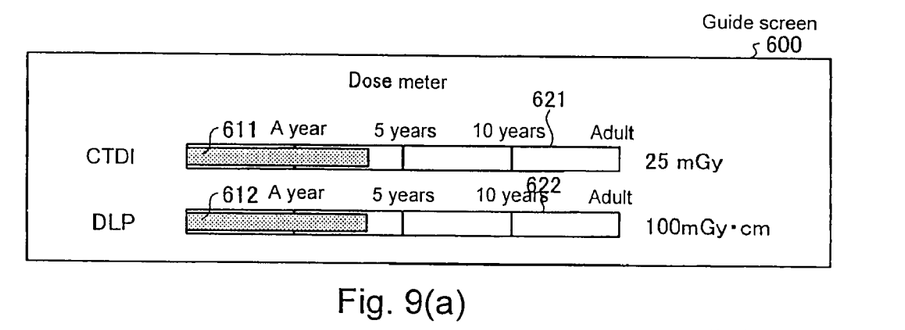
Figure 9B:
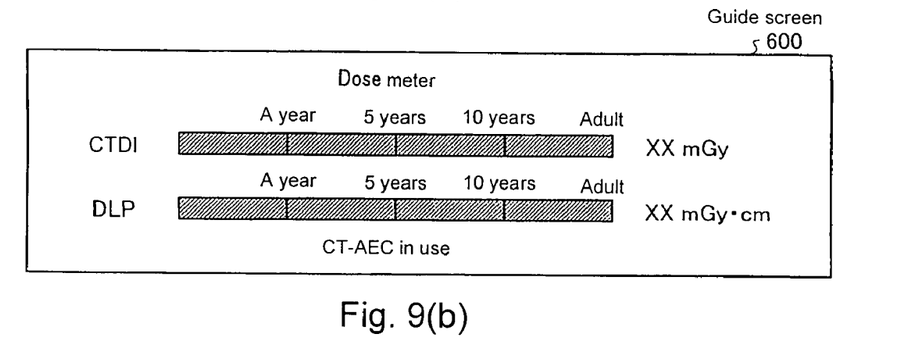

FIGS. 9(a) and 9(b) are schematic diagrams indicating examples of the guide screen displayed when the expert plan is made. For example, the scan plan assistance unit 200 related to the third exemplary embodiment calculates CTDI and DLP as values of the exposure dose and outputs a meter 611 indicating an amount of the calculated CTDI, a meter 612 indicating an amount of the calculated DLP as shown in FIG. 9(*a*).

In the example shown by FIG. 9(*a*), the scan plan assistance unit 200 outputs a scale 621 of CTDI and a scale 622 DLP each of which indicates age change of reference dose on the basis of the reference dose stored in the reference dose storage unit 203 and superimposes the meter 611 of CTDI and the meter 612 of DLP, each of which indicates amount of the exposure dose on these scales.

In this manner, the operator can intuitively perceive whether the exposure dose corresponding to the set scan condition is suitable in regard to the age of the subject. For example, in the case of FIG. 9(*a*), it can be perceived that the exposure dose corresponding to the set scan condition is suitable for a subject who is older than 1 year old and younger than 5 years old.

As mentioned above, in the third exemplary embodiment, the scan plan assistance unit 200 outputs not only the exposure dose corresponding to the set scan condition, but also age information in accordance with the exposure dose by reference to the reference dose information when the operator sets scan conditions. In this manner, attribute information that is appropriate to a set scan condition can be provided to the operator as a reference information when the operator makes an expert plan.

In addition, in above explanation, the age information is displayed on the guide screen 600. However, other attribute information stored in the reference dose storage unit 203, such as for example weight or height, can be displayed on the guide screen 600.

By the way, for example, in case an exposure reduction function by which exposure dose is automatically adjusted in accordance with the subject part for examination is used, because of unknown actual exposure dose, the bar charts are not displayed on the guide screen 600 and a message indicating that CT-AEC is in use is displayed as shown in FIG. 9(*b*). In addition, in this case, exposure dose of an ideal state by set SD may be calculated and displayed.

Furthermore, in above mentioned exemplary embodiments, an exposure dose value is based on recommended standard of accredited organizations or academic conference for example ICRP, IEC or ACR. However the present invention is not limited in this manner, the other standards, for example in accordance with exposure dose at which skin can be burned or ones hair comes off by can be employed. In addition, the operator may be informed by the warning provided in a phased manner by checking the exposure dose in a phased manner.

Numerous modification and variations of the present invention are possible in light of the above teachings. It is therefore to be understood that within the scope of the appended claims, the invention may be practiced otherwise than as specifically described herein.

What is claimed is:

1. An X-ray CT apparatus, comprising:
    a scan plan setting unit configured to set a scan condition for an element of a scan plan for an actual subject;
    a reference dose storage unit configured to store a reference dose information table including a relation between body attribute information for each of a plurality of potential subjects and reference doses to be referenced for exposure, wherein the body attribution information is at least one of age, weight, and height of each potential subject, and wherein the reference doses are indicated by CTDI (Computed Tomography Dose Index), DLP (Dose Length Product), and sum of DLP;
    an exposure dose calculation unit configured to calculate an exposure dose corresponding to the scan condition, before transmitting X-rays corresponding to the scan condition;
    a dose decision unit configured to decide whether the calculated exposure dose exceeds the reference dose corresponding to at least one of age, weight, and height of the actual subject, based on the reference dose information table stored in the reference dose storage unit, to produce a dose decision, before transmitting X-rays corresponding to the scan condition;
    an image generation unit configured to generate an image based on data acquired by transmitting the X-rays corresponding to the scan condition, when the dose decision unit decides that the calculated exposure dose does not exceed the reference dose; and
    a dose warning unit configured to output a warning message before transmitting any X-rays corresponding to the scan condition, when the dose decision unit decides that the calculated exposure dose exceeds the reference dose.

2. The X-ray CT apparatus according to claim 1, further comprising:
    a scan plan information storage unit configured to store the scan condition related to the element of the scan plan for an independent X-ray CT scan, wherein
    the scan plan setting unit is further configured to select the element of the scan plan and change the scan condition related to the element of the scan plan, and
    the exposure dose calculation unit is further configured to calculate the exposure dose corresponding to the element of the scan plan in accordance with the change of the scan condition, before transmitting X-rays corresponding to the scan condition.

3. The X-ray CT apparatus according to claim 1, wherein the scan plan setting unit is further configured to accept an input of a readjustment of the scan condition or an acceptance of the scan condition, when the dose warning unit outputs the warning message.

4. The X-ray CT apparatus according to claim 1, wherein the scan plan setting unit is further configured to output a bar chart indicating an amount of the calculated exposure dose in comparison with the reference dose corresponding to the body attribute information of the subject, when the dose warning unit outputs the warning message.

5. The X-ray CT apparatus according to claim 1, wherein the scan plan setting unit is further configured to output history information related to a total sum of an exposure dose exposed to the subject, when the dose warning unit outputs the warning message.

6. The X-ray CT apparatus according to claim 1, wherein the scan plan setting unit is further configured to display a dose display button including the calculated exposure dose, and change a displaying manner of the dose display button, when the dose decision indicates that the calculated exposure dose exceeds the reference dose corresponding to the body attribute information of the subject.

7. The X-ray CT apparatus according to claim 6, wherein the dose warning unit is configured to output the warning message when the dose display button is pushed by an operator.

8. The X-ray CT apparatus according to claim 1, further comprising a display unit configured to display an amount of the calculated exposure dose in comparison with the reference dose corresponding to the body attribute information of the subject.

9. The X-ray CT apparatus according to claim 8, wherein the display unit is further configured to display the plurality of reference doses corresponding to the plurality of reference body attribute information.

10. The X-ray CT apparatus according to claim 9, wherein the display unit is further configured to display the plurality of the reference doses in accordance with input body attribute information input by an operator.

11. The X-ray CT apparatus according to claim 1, wherein the reference dose is based on reference values of exposure doses recommended by academic conferences.

12. The X-ray CT apparatus according to claim 1, wherein the reference dose storage unit is further configured to store the reference dose information table including a relation between each of a plurality of bodily components for each of the plurality of potential subjects and reference doses to be referenced for exposure, based on the body attribute information of each of the plurality of potential subjects.

13. A method for scan plan assistance, comprising:
setting a scan condition for an element of a scan plan for an actual subject;
storing a reference dose information table including a relation between body attribute information for each of a plurality of potential subjects and reference doses to be referenced for exposure, wherein the body attribution information is at least one of age, weight, and height of each potential subject, and wherein the reference doses are indicated by CTDI (Computed Tomography Dose Index), DLP (Dose Length Product), and sum of DLP;
calculating, by a processing unit, an exposure dose corresponding to the scan condition, before transmitting X-rays corresponding to the scan condition;
deciding whether the calculated exposure dose exceeds the reference dose corresponding to at least one of age, weight, and height of the actual subject stored in the storing step based on the reference dose information table, to produce a dose decision, before transmitting X-rays corresponding to the scan condition;
generating an image based on data acquired by transmitting the X-rays corresponding to the scan condition, when the deciding step decides that the calculated exposure dose does not exceed the reference dose information; and
outputting a warning message before transmitting any X-rays corresponding to the scan condition, when the deciding step decides that the calculated exposure dose exceeds the reference dose.

14. The method for scan plan assistance according to claim 13, further comprising:
storing the scan condition related to the element of the scan plan for an independent X-ray CT scan, wherein
the setting step further includes selecting the element of the scan plan and changing the scan condition related to the element of the scan plan, and
the calculating step further includes calculating the exposure dose corresponding to the element of the scan plan in accordance with the change of the scan condition, before transmitting X-rays corresponding to the scan condition.

15. The method for scan plan assistance according to claim 13, further comprising inputting a readjustment of the scan condition or an acceptance of the scan condition, when the warning message is output.

16. The method for scan plan assistance according to claim 13, further comprising outputting a bar chart indicating amount of the calculated exposure dose in comparison with the reference dose corresponding to the body attribute information of the subject, when the warning message is displayed.

17. The method for scan plan assistance according to claim 13, further comprising outputting history information related to a total sum of an exposure dose exposed to the subject, when the warning message is output.

18. The method for scan plan assistance according to claim 13, further comprising:
displaying a dose display button including the calculated exposure dose; and
changing a displaying manner of the dose display button, when the dose decision indicates that the calculated exposure dose exceeds the reference dose corresponding to the body attribute information of the subject.

19. The method for scan plan assistance according to claim 18, further comprising outputting the warning message when the dose display button is pushed by an operator.

20. The method for scan plan assistance according to claim 13, further comprising displaying an amount of the calculated exposure dose in comparison with the reference dose corresponding to the body attribute information of the subject.

21. The method for scan plan assistance according to claim 20, further comprising displaying the plurality of the reference doses corresponding to the plurality of reference body attribute information.

22. The method for scan plan assistance according to claim 21, further comprising displaying the plurality of the reference doses in accordance with input body attribute information input by an operator.

* * * * *